United States Patent [19]

Payne et al.

[11] Patent Number: 5,352,661
[45] Date of Patent: Oct. 4, 1994

[54] BACILLUS THURINGIENSIS ISOLATE DENOTED B.T. PS81GG, ACTIVE AGAINST LEPIDOPTERAN PESTS, AND A GENE ENCODING A LEPIDOPTERAN-ACTIVE TOXIN

[75] Inventors: Jewel Payne; August J. Sick, both of San Diego; Mark Thompson, Del Mar, all of Calif.

[73] Assignee: Mycogen Corporation, San Diego, Calif.

[21] Appl. No.: 920,085

[22] Filed: Jul. 27, 1992

Related U.S. Application Data

[62] Division of Ser. No. 265,731, Nov. 1, 1988, Pat. No. 5,169,629.

[51] Int. Cl.⁵ ............... A61K 37/00; A01N 63/00; C07H 19/00; C07H 17/00
[52] U.S. Cl. ............... 424/93.2; 424/93.21; 435/69.1; 435/242; 435/832; 536/22.1; 536/23.1; 536/23.2; 536/23.7; 536/23.71; 514/12
[58] Field of Search ............... 514/12; 424/93 L; 435/69.1, 832, 242; 536/22.1, 23.1, 23.2, 23.7, 23.71

[56] References Cited

PUBLICATIONS

Whiteley et al. "Molecular Biology of Parasporal Crystal Body . . . " Ann. Rev. Microbiol. 40:549–76 1986.
Prefontaine et al. "Use of Oligonucleotide Probes . . . " App. Env. Microbiol. Dec. 1987 pp. 2808–2814.
Glover "The principles of cloning DNA" from *Gene Cloning* 1985 pp. 1–19.

*Primary Examiner*—Robert A. Wax
*Assistant Examiner*—Hyosuk Kim
*Attorney, Agent, or Firm*—Saliwanchik & Saliwanchik

[57] ABSTRACT

A novel B.t. isolate with activity against lepidopteran insects is disclosed. This isolate is highly active against the beet armyworm. A gene from this isolate has been cloned. The DNA encoding the B.t. toxin can be used to transform various prokaryotic and eukaryotic microbes to express the B.t. toxin. These recombinant microbes can be used to control lepidopteran insects in various environments.

5 Claims, 1 Drawing Sheet

Figure 1

A. *Bacillus thuringiensis* PS81GG uncut
B. *Bacillus thuringiensis* PS81GG cut with HindIII
C. *Bacillus thuringiensis* HD-1 uncut
D. *Bacillus thuringiensis* HD-1 cut with HindIII

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3531 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: BACILLUS THURINGIENSIS
        ( B ) STRAIN: KURSTAKI
        ( C ) INDIVIDUAL ISOLATE: PS81GG ( v i i ) IMMEDIATE SOURCE:
        ( A ) LIBRARY: LAMBDAGEM (TM) - 11 LIBRARY OF AUGUST SICK
        ( B ) CLONE: 81GG ( x i ) SEQUENCE DESCRIPTION: SEQ ID NO:1:

```
ATGGATAACA ATCCGAACAT CAATGAATGC ATTCCTTATA ATTGTTTAAG TAACCCTGAA          60
GTAGAAGTAT TAGGTGGAGA AAGAATAGAA ACTGGTTACA CCCCAATCGA TATTTCCTTG         120
TCGCTAACGC AATTTCTTTT GAGTGAATTT GTTCCCGGTG CTGGATTTGT GTTAGGACTA         180
GTTGATATAA TATGGGGAAT TTTTGGTCCC TCTCAATGGG ACGCATTTCT TGTACAAATT         240
```

-continued

```
GAACAGTTAA TTAACCAAAG AATAGAAGAA TTCGCTAGGA ACCAAGCCAT TTCTAGATTA    300
GAAGGACTAA GCAATCTTTA TCAAATTTAC GCAGAATCTT TTAGAGAGTG GAAGCAGAT    360
CCTACTAATC CAGCATTAAG AGAAGAGATG CGTATTCAAT TCAATGACAT GAACAGTGCC    420
CTTACAACCG CTATTCCTCT TTTGGCAGTT CAAAATTATC AAGTTCCTCT TTTATCAGTA    480
TATGTTCAAG CTGCAAATTT ACATTTATCA GTTTTGAGAG ATGTTTCAGT GTTTGGACAA    540
AGGTGGGGAT TTGATGCCGC GACTATCAAT AGTCGTTATA ATGATTTAAC TAGGCTTATT    600
GGCAACTATA CAGATTATGC TGTACGCTGG TACAATACGG GATTAGAACG TGTATGGGGA    660
CCGGATTCTA GAGATTGGGT AAGGTATAAT CAATTTAGAA GAGAATTAAC ACTAACTGTA    720
TTAGATATCG TTGCTCTGTT CCCGAATTAT GATAGTAGAA GATATCCAAT TCGAACAGTT    780
TCCCAATTAA CAAGAGAAAT TTATACAAAC CCAGTATTAG AAAATTTTGA TGGTAGTTTT    840
CGAGGCTCGG CTCAGGGCAT AGAAAGAAGT ATTAGGAGTC ACATTTGAT GGATATACTT     900
AACAGTATAA CCATCTATAC GGATGCTCAT AGGGGTTATT ATTATTGGTC AGGGCATCAA    960
ATAATGGCTT CTCCTGTCGG TTTTTCGGGG CCAGAATTCA CGTTTCCGCT ATATGGAACC   1020
ATGGGAAATG CAGCTCCACA ACAACGTATT GTTGCTCAAC TAGGTCAGGG CGTGTATAGA   1080
ACATTATCCT CTACTTTTTA TAGAAGACCT TTTAATATAG GATAAATAA TCAACAACTA    1140
TCTGTTCTTG ACGGGACAGA ATTTGCTTAT GGAACCTCCT CAAATTTGCC ATCCGCTGTA   1200
TACAGAAAAA GCGGAACGGT AGATTCGCTG GATGAAATAC CACCACAGAA TAACAACGTG   1260
CCACCTAGGC AAGGATTTAG TCATCGATTA AGCCATGTTT CAATGTTTCG TTCAGGCTCT   1320
AGTAGTAGTG TAAGTATAAT AAGAGCTCCT ATGTTCTCTT GGATACATCG TAGTGCTGAA   1380
TTTAATAATA TAATTGCATC GGATAGTATT ACTCAAATCC CTGCAGTGAA GGGAAACTTT   1440
CTTTTTAATG GTTCTGTAAT TTCAGGACCA GGATTTACTG GTGGGGACTT AGTTAGATTA   1500
AATAGTAGTG GAAATAACAT TCAGAATAGA GGGTATATTG AAGTTCCAAT TCACTTCCCA   1560
TCGACATCTA CCAGATATCG AGTTCGTGTA CGGTATGCTT CTGTAACCCC GATTCACCTC   1620
AACGTTAATT GGGGTAATTC ATCCATTTTT TCCAATACAG TACCAGCTAC AGCTACGTCA   1680
TTAGATAATC TACAATCAAG TGATTTTGGT TATTTTGAAA GTGCCAATGC TTTTACATCT   1740
TCATTAGGTA ATATAGTAGG TGTTAGAAAT TTAGTGGGA CTGCAGGAGT GATAATAGAC    1800
AGATTTGAAT TTATTCCAGT TACTGCAACA CTCGAGGCTG AATATAATCT GGAAAGAGCG   1860
CAGAAGGCGG TGAATGCGCT GTTTACGTCT ACAAACCAAC TAGGGCTAAA AACAAATGTA   1920
ACGGATTATC ATATTGATCA AGTGTCCAAT TTAGTTACGT ATTTATCGGA TGAATTTTGT   1980
CTGGATGAAA AGCGAGAATT GTCCGAGAAA GTCAAACATG CGAAGCGACT CAGTGATGAA   2040
CGCAATTTAC TCCAAGATTC AAATTTCAAA GACATTAATA GGCAACCAGA ACGTGGGTGG   2100
GGCGGAAGTA CAGGGATTAC CATCCAAGGA GGGGATGACG TATTTAAAGA AAATTACGTC   2160
ACACTATCAG GTACCTTTGA TGAGTGCTAT CCAACATATT TGTATCAAAA AATCGATGAA   2220
TCAAAATTAA AAGCCTTTAC CCGTTATCAA TTAAGAGGGT ATATCGAAGA TAGTCAAGAC   2280
TTAGAAATCT ATTTAATTCG CTACAATGCA AAACATGAAA CAGTAAATGT GCCAGGTACG   2340
GGTTCCTTAT GGCCGCTTTC AGCCCAAAGT CCAATCGGAA AGTGTGGAGA GCCAATCGA    2400
TGCGCGCCAC ACCTTGAATG GAATCCTGAC TTAGATTGTT CGTGTAGGGA TGGAGAAAAG   2460
TGTGCCCATC ATTCGCATCA TTTCTCCTTA GACATTGATG TAGGATGTAC AGACTTAAAT   2520
GAGGACCTAG GTGTATGGGT GATCTTTAAG ATTAAGACGC AAGATGGGCA CGCAAGACTA   2580
GGGAATCTAG AGTTTCTCGA AGAGAAACCA TTAGTAGGAG AAGCGCTAGC TCGTGTGAAA   2640
AGAGCGGAGA AAAAATGGAG AGACAAACGT GAAAAATTGG AATGGGAAAC AAATATCGTT   2700
```

-continued

```
TATAAAGAGG CAAAAGAATC TGTAGATGCT TTATTTGTAA ACTCTCAATA TGATCAATTA    2760
CAAGCGGATA CGAATATTGC CATGATTCAT GCGGCAGATA AACGTGTTCA TAGCATTCGA    2820
GAAGCTTATC TGCCTGAGCT GTCTGTGATT CCGGGTGTCA ATGCGGCTAT TTTTGAAGAA    2880
TTAGAAGGGC GTATTTTCAC TGCATTCTCC CTATATGATG CGAGAAATGT CATTAAAAAT    2940
GGTGATTTTA ATAATGGCTT ATCCTGCTGG AACGTGAAAG GGCATGTAGA TGTAGAAGAA    3000
CAAAACAACC AACGTTCGGT CCTTGTTGTT CCGGAATGGG AAGCAGAAGT GTCACAAGAA    3060
GTTCGTGTCT GTCCGGGTCG TGGCTATATC CTTCGTGTCA CAGCGTACAA GGAGGGATAT    3120
GGAGAAGGTT GCGTAACCAT TCATGAGATC GAGAACAATA CAGACGAACT GAAGTTTAGC    3180
AACTGCGTAG AAGAGGAAAT CTATCCAAAT AACACGGTAA CGTGTAATGA TTATACTGTA    3240
AATCAAGAAG AATACGGAGG TGCGTACACT TCTCGTAATC GAGGATATAA CGAAGCTCCT    3300
TCCGTACCAG CTGATTATGC GTCAGTCTAT GAAGAAAAAT CGTATACAGA TGGACGAAGA    3360
GAGAATCCTT GTGAATTTAA CAGAGGGTAT AGGGATTACA CGCCACTACC AGTTGGTTAT    3420
GTGACAAAAG AATTAGAATA CTTCCCAGAA ACCGATAAGG TATGGATTGA GATTGGAGAA    3480
ACGGAAGGAA CATTTATCGT GGACAGCGTG GAATTACTCC TTATGGAGGA A              3531
```

( 2 ) INFORMATION FOR SEQ ID NO:2:

( i ) SEQUENCE CHARACTERISTICS:
        ( A ) LENGTH: 1177 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: BACILLUS THURINGIENSIS
        ( B ) STRAIN: KURSTAKI
        ( C ) INDIVIDUAL ISOLATE: PS81GG ( v i i ) IMMEDIATE SOURCE:
        ( A ) LIBRARY: LAMBDAGEM (TM) - 11 LIBRARY OF AUGUST SICK
        ( B ) CLONE: 81GG ( x i ) SEQUENCE DESCRIPTION: SEQ ID NO:2:

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140
```

-continued

| | | | | | | | | | | | | | | | |
|---|---|---|---|---|---|---|---|---|---|---|---|---|---|---|---|
| Ile 145 | Pro | Leu | Leu | Ala | Val 150 | Gln | Asn | Tyr | Gln | Val 155 | Pro | Leu | Leu | Ser | Val 160 |
| Tyr | Val | Gln | Ala | Ala 165 | Asn | Leu | His | Leu | Ser 170 | Val | Leu | Arg | Asp | Val 175 | Ser |
| Val | Phe | Gly | Gln 180 | Arg | Trp | Gly | Phe | Asp 185 | Ala | Ala | Thr | Ile | Asn 190 | Ser | Arg |
| Tyr | Asn | Asp 195 | Leu | Thr | Arg | Leu | Ile 200 | Gly | Asn | Tyr | Thr | Asp 205 | Tyr | Ala | Val |
| Arg | Trp 210 | Tyr | Asn | Thr | Gly | Leu 215 | Glu | Arg | Val | Trp | Gly 220 | Pro | Asp | Ser | Arg |
| Asp 225 | Trp | Val | Arg | Tyr | Asn 230 | Gln | Phe | Arg | Arg | Glu 235 | Leu | Thr | Leu | Thr | Val 240 |
| Leu | Asp | Ile | Val | Ala 245 | Leu | Phe | Pro | Asn | Tyr 250 | Asp | Ser | Arg | Arg | Tyr 255 | Pro |
| Ile | Arg | Thr | Val 260 | Ser | Gln | Leu | Thr | Arg 265 | Glu | Ile | Tyr | Thr | Asn 270 | Pro | Val |
| Leu | Glu | Asn 275 | Phe | Asp | Gly | Ser | Phe 280 | Arg | Gly | Ser | Ala | Gln 285 | Gly | Ile | Glu |
| Arg | Ser 290 | Ile | Arg | Ser | Pro | His 295 | Leu | Met | Asp | Ile | Leu 300 | Asn | Ser | Ile | Thr |
| Ile 305 | Tyr | Thr | Asp | Ala | His 310 | Arg | Gly | Tyr | Tyr | Tyr 315 | Trp | Ser | Gly | His | Gln 320 |
| Ile | Met | Ala | Ser | Pro 325 | Val | Gly | Phe | Ser | Gly 330 | Pro | Glu | Phe | Thr | Phe 335 | Pro |
| Leu | Tyr | Gly | Thr 340 | Met | Gly | Asn | Ala | Ala 345 | Pro | Gln | Gln | Arg | Ile 350 | Val | Ala |
| Gln | Leu | Gly 355 | Gln | Gly | Val | Tyr | Arg 360 | Thr | Leu | Ser | Ser | Thr 365 | Phe | Tyr | Arg |
| Arg | Pro 370 | Phe | Asn | Ile | Gly | Ile 375 | Asn | Asn | Gln | Gln | Leu 380 | Ser | Val | Leu | Asp |
| Gly 385 | Thr | Glu | Phe | Ala | Tyr 390 | Gly | Thr | Ser | Ser | Asn 395 | Leu | Pro | Ser | Ala | Val 400 |
| Tyr | Arg | Lys | Ser | Gly 405 | Thr | Val | Asp | Ser | Leu 410 | Asp | Glu | Ile | Pro | Pro 415 | Gln |
| Asn | Asn | Asn | Val 420 | Pro | Pro | Arg | Gln | Gly 425 | Phe | Ser | His | Arg | Leu 430 | Ser | His |
| Val | Ser | Met 435 | Phe | Arg | Ser | Gly | Ser 440 | Ser | Ser | Val | Ser | Ile 445 | Ile | Arg |
| Ala | Pro 450 | Met | Phe | Ser | Trp | Ile 455 | His | Arg | Ser | Ala | Glu 460 | Phe | Asn | Asn | Ile |
| Ile 465 | Ala | Ser | Asp | Ser | Ile 470 | Thr | Gln | Ile | Pro | Ala 475 | Val | Lys | Gly | Asn | Phe 480 |
| Leu | Phe | Asn | Gly | Ser 485 | Val | Ile | Ser | Gly | Pro 490 | Gly | Phe | Thr | Gly | Gly 495 | Asp |
| Leu | Val | Arg | Leu 500 | Asn | Ser | Ser | Gly | Asn 505 | Asn | Ile | Gln | Asn | Arg 510 | Gly | Tyr |
| Ile | Glu | Val 515 | Pro | Ile | His | Phe | Pro 520 | Ser | Thr | Ser | Thr | Arg 525 | Tyr | Arg | Val |
| Arg | Val 530 | Arg | Tyr | Ala | Ser | Val 535 | Thr | Pro | Ile | His | Leu 540 | Asn | Val | Asn | Trp |
| Gly 545 | Asn | Ser | Ser | Ile | Phe 550 | Ser | Asn | Thr | Val | Pro 555 | Ala | Thr | Ala | Thr | Ser 560 |
| Leu | Asp | Asn | Leu | Gln 565 | Ser | Ser | Asp | Phe | Gly 570 | Tyr | Phe | Glu | Ser | Ala 575 | Asn |
| Ala | Phe | Thr | Ser | Ser | Leu | Gly | Asn | Ile | Val | Gly | Val | Arg | Asn | Phe | Ser |

|     |     |     | 580 |     |     |     |     | 585 |     |     |     |     | 590 |     |     |
| --- | --- | --- | --- | --- | --- | --- | --- | --- | --- | --- | --- | --- | --- | --- | --- |
| Gly | Thr | Ala | Gly | Val | Ile | Ile | Asp | Arg | Phe | Glu | Phe | Ile | Pro | Val | Thr |
|     |     |     | 595 |     |     |     |     | 600 |     |     |     |     | 605 |     |     |
| Ala | Thr | Leu | Glu | Ala | Glu | Tyr | Asn | Leu | Glu | Arg | Ala | Gln | Lys | Ala | Val |
|     |     |     | 610 |     |     |     |     | 615 |     |     |     |     | 620 |     |     |
| Asn | Ala | Leu | Phe | Thr | Ser | Thr | Asn | Gln | Leu | Gly | Leu | Lys | Thr | Asn | Val |
| 625 |     |     |     |     |     | 630 |     |     |     |     | 635 |     |     |     | 640 |
| Thr | Asp | Tyr | His | Ile | Asp | Gln | Val | Ser | Asn | Leu | Val | Thr | Tyr | Leu | Ser |
|     |     |     |     | 645 |     |     |     |     | 650 |     |     |     |     | 655 |     |
| Asp | Glu | Phe | Cys | Leu | Asp | Glu | Lys | Arg | Glu | Leu | Ser | Glu | Lys | Val | Lys |
|     |     |     | 660 |     |     |     |     | 665 |     |     |     |     | 670 |     |     |
| His | Ala | Lys | Arg | Leu | Ser | Asp | Glu | Arg | Asn | Leu | Leu | Gln | Asp | Ser | Asn |
|     |     |     | 675 |     |     |     |     | 680 |     |     |     |     | 685 |     |     |
| Phe | Lys | Asp | Ile | Asn | Arg | Gln | Pro | Glu | Arg | Gly | Trp | Gly | Gly | Ser | Thr |
|     |     | 690 |     |     |     |     | 695 |     |     |     |     | 700 |     |     |     |
| Gly | Ile | Thr | Ile | Gln | Gly | Gly | Asp | Asp | Val | Phe | Lys | Glu | Asn | Tyr | Val |
| 705 |     |     |     |     |     | 710 |     |     |     |     | 715 |     |     |     | 720 |
| Thr | Leu | Ser | Gly | Thr | Phe | Asp | Glu | Cys | Tyr | Pro | Thr | Tyr | Leu | Tyr | Gln |
|     |     |     |     | 725 |     |     |     |     | 730 |     |     |     |     | 735 |     |
| Lys | Ile | Asp | Glu | Ser | Lys | Leu | Lys | Ala | Phe | Thr | Arg | Tyr | Gln | Leu | Arg |
|     |     |     | 740 |     |     |     |     | 745 |     |     |     |     | 750 |     |     |
| Gly | Tyr | Ile | Glu | Asp | Ser | Gln | Asp | Leu | Glu | Ile | Tyr | Leu | Ile | Arg | Tyr |
|     |     |     | 755 |     |     |     |     | 760 |     |     |     |     | 765 |     |     |
| Asn | Ala | Lys | His | Glu | Thr | Val | Asn | Val | Pro | Gly | Thr | Gly | Ser | Leu | Trp |
|     |     | 770 |     |     |     |     | 775 |     |     |     |     | 780 |     |     |     |
| Pro | Leu | Ser | Ala | Gln | Ser | Pro | Ile | Gly | Lys | Cys | Gly | Glu | Pro | Asn | Arg |
| 785 |     |     |     |     | 790 |     |     |     |     | 795 |     |     |     |     | 800 |
| Cys | Ala | Pro | His | Leu | Glu | Trp | Asn | Pro | Asp | Leu | Asp | Cys | Ser | Cys | Arg |
|     |     |     |     | 805 |     |     |     |     | 810 |     |     |     |     | 815 |     |
| Asp | Gly | Glu | Lys | Cys | Ala | His | His | Ser | His | His | Phe | Ser | Leu | Asp | Ile |
|     |     |     | 820 |     |     |     |     | 825 |     |     |     |     | 830 |     |     |
| Asp | Val | Gly | Cys | Thr | Asp | Leu | Asn | Glu | Asp | Leu | Gly | Val | Trp | Val | Ile |
|     |     |     | 835 |     |     |     |     | 840 |     |     |     |     | 845 |     |     |
| Phe | Lys | Ile | Lys | Thr | Gln | Asp | Gly | His | Ala | Arg | Leu | Gly | Asn | Leu | Glu |
|     |     |     | 850 |     |     |     |     | 855 |     |     |     |     | 860 |     |     |
| Phe | Leu | Glu | Glu | Lys | Pro | Leu | Val | Gly | Glu | Ala | Leu | Ala | Arg | Val | Lys |
| 865 |     |     |     |     | 870 |     |     |     |     | 875 |     |     |     |     | 880 |
| Arg | Ala | Glu | Lys | Lys | Trp | Arg | Asp | Lys | Arg | Glu | Lys | Leu | Glu | Trp | Glu |
|     |     |     |     | 885 |     |     |     |     | 890 |     |     |     |     | 895 |     |
| Thr | Asn | Ile | Val | Tyr | Lys | Glu | Ala | Lys | Glu | Ser | Val | Asp | Ala | Leu | Phe |
|     |     |     | 900 |     |     |     |     | 905 |     |     |     |     | 910 |     |     |
| Val | Asn | Ser | Gln | Tyr | Asp | Gln | Leu | Gln | Ala | Asp | Thr | Asn | Ile | Ala | Met |
|     |     | 915 |     |     |     |     | 920 |     |     |     |     | 925 |     |     |     |
| Ile | His | Ala | Ala | Asp | Lys | Arg | Val | His | Ser | Ile | Arg | Glu | Ala | Tyr | Leu |
| 930 |     |     |     |     | 935 |     |     |     |     | 940 |     |     |     |     |     |
| Pro | Glu | Leu | Ser | Val | Ile | Pro | Gly | Val | Asn | Ala | Ala | Ile | Phe | Glu | Glu |
| 945 |     |     |     | 950 |     |     |     |     | 955 |     |     |     |     |     | 960 |
| Leu | Glu | Gly | Arg | Ile | Phe | Thr | Ala | Phe | Ser | Leu | Tyr | Asp | Ala | Arg | Asn |
|     |     |     |     | 965 |     |     |     |     | 970 |     |     |     |     | 975 |     |
| Val | Ile | Lys | Asn | Gly | Asp | Phe | Asn | Asn | Gly | Leu | Ser | Cys | Trp | Asn | Val |
|     |     |     | 980 |     |     |     |     | 985 |     |     |     |     | 990 |     |     |
| Lys | Gly | His | Val | Asp | Val | Glu | Glu | Gln | Asn | Asn | Gln | Arg | Ser | Val | Leu |
|     |     |     | 995 |     |     |     |     | 1000|     |     |     |     | 1005|     |     |
| Val | Val | Pro | Glu | Trp | Glu | Ala | Glu | Val | Ser | Gln | Glu | Val | Arg | Val | Cys |
|     |     |     | 1010|     |     |     |     | 1015|     |     |     |     | 1020|     |     |

```
Pro Gly Arg Gly Tyr Ile Leu Arg Val Thr Ala Tyr Lys Glu Gly Tyr
1025                1030            1035                    1040

Gly Glu Gly Cys Val Thr Ile His Glu Ile Glu Asn Asn Thr Asp Glu
                1045            1050                1055

Leu Lys Phe Ser Asn Cys Val Glu Glu Glu Ile Tyr Pro Asn Asn Thr
            1060            1065            1070

Val Thr Cys Asn Asp Tyr Thr Val Asn Gln Glu Glu Tyr Gly Gly Ala
        1075            1080            1085

Tyr Thr Ser Arg Asn Arg Gly Tyr Asn Glu Ala Pro Ser Val Pro Ala
    1090            1095            1100

Asp Tyr Ala Ser Val Tyr Glu Glu Lys Ser Tyr Thr Asp Gly Arg Arg
1105            1110            1115                    1120

Glu Asn Pro Cys Glu Phe Asn Arg Gly Tyr Arg Asp Tyr Thr Pro Leu
            1125            1130            1135

Pro Val Gly Tyr Val Thr Lys Glu Leu Glu Tyr Phe Pro Glu Thr Asp
            1140            1145            1150

Lys Val Trp Ile Glu Ile Gly Glu Thr Glu Gly Thr Phe Ile Val Asp
        1155            1160            1165

Ser Val Glu Leu Leu Leu Met Glu Glu
    1170            1175
```

BACILLUS THURINGIENSIS ISOLATE DENOTED B.T. PS81GG, ACTIVE AGAINST LEPIDOPTERAN PESTS, AND A GENE ENCODING A LEPIDOPTERAN-ACTIVE TOXIN

This is a division of application Ser. No. 07/265,731 filed Nov. 1, 1988 which is now U.S. Pat. No. 5,169,629.

BACKGROUND OF THE INVENTION

(1) Microbial Pesticides

The most widely used microbial pesticides are derived from the bacterium *Bacillus thuringiensis*. This bacterial agent is used to control a wide range of leaf-eating caterpillars, and mosquitos. *Bacillus thuringiensis* produces a proteinaceous paraspore or crystal which is toxic upon ingestion by a susceptible insect host. For example, *B. thuringiensis* var. kurstaki HD-1 produces a crystal called a delta toxin which is toxic to the larvae of a number of lepidopteran insects. The cloning and expression of this B.t. crystal protein gene in *Escherichia coli* has been described in the published literature (Schnepf, H. E. and Whirely, H. R. [1981]Proc. Natl. Acad. Sci. USA 78:2893-2897). U.S. Pat. No. 4,448,885 and U.S. Pat. No. 4,467,036 both disclose the expression of B.t. crystal protein in *E. coli*.

(2) Lepidopteran Pests

The beet armyworm (BAW) *Spodoptera exigua* is a widely distributed noctuid moth that attacks a broad range of field and vegetable crops. This economically important species originated in Asia, but is now found in many parts of the world including the United States.

The plants attacked by BAW include beets, peanuts, alfalfa, lettuce, asparagus, tomatoes, potatoes, corn, onions, peas, cotton, citrus, mallow, and even certain wild grasses. It is also a pest on ornamentals and floriculture crops, such as carnations and chrysanthemums. Larvae will feed on the leaves, stems, buds, and sometimes the roots of host plants. Heavy infestations can lead to complete defoliation of fields of a crop, such as table beets.

The female oviposits egg masses of about 80 eggs on the host plant foliage. These egg masses are covered with hairs and scales from the body of the female. An average of 500 to 600 eggs may be deposited over a 4 to 10 day period. Larvae hatch in 2 to 5 days and begin feeding on the foliage. Young larvae will feed in growing tips of the plant and developing buds, while older larvae are less discriminating, feeding on older foliage as well. The five larval instars take about 3 weeks to complete, at which time the mature larva drops to the ground and pupates in the soil. In the warmer parts of its range the BAW passes through four generations per year.

This species is generally considered to be difficult to control in various crop situations. Methomyl (Lannate) is commonly used to control this pest in lettuce and other field crops. However, resistance to methomyl has been reported in populations exposed to heavy use of this chemical (Yoshida and Parella [1987]). Consequently, there is a need to develop alternative control strategies for this important pest.

Another aspect of the use of broad spectrum materials like Lannate for BAW control is secondary pest outbreaks. This is the disruptive influence of a nonselective chemical on natural control agents of other pests in a given crop. In tomatoes, chrysanthemums, and other crops, where leaf miners can be a problem, the use of Lannate severely depresses populations of the natural enemies of the leafminers. With removal of leafminer parasites, the leafminers can build to very high population levels and cause severe damage.

The discovery and use of a novel *Bacillus thuringiensis* isolate with good activity against BAW is a distinct improvement in the control of this lepidopteran pest.

BRIEF SUMMARY OF THE INVENTION

The subject invention concerns a novel *Bacillus thuringiensis* isolate designated B.t. PS81GG which has activity against lepidopteran pests. It is highly active against the beet armyworm (BAW).

The subject invention also includes mutants of B.t. PS81GG which are also active against lepidopteran pests.

Also disclosed and claimed is the novel toxin gene from the novel isolate. This toxin gene can be transferred to suitable hosts via a plasmid vector.

Specifically, the invention comprises a novel B.t. isolate denoted B.t. PS81GG, and mutants thereof, and a novel delta endotoxin gene which encodes a 133,156 dalton protein which is active against lepidopteran pests.

SEQ. ID NO. 1 discloses the DNA encoding the toxin of PS81GG.

SEQ. ID NO. 2 discloses the amino acid sequence of the toxin of PS81GG.

BRIEF DESCRIPTION OF THE DRAWING

FIG. 1—Agarose gel electrophoresis of plasmid preparations from B.t. PS81GG and B.t. HD-1.

DETAILED DISCLOSURE OF THE INVENTION

The novel toxin gene of the subject invention was obtained from a novel lepidopteran-active *B. thuringiensis* (B.t.) isolate designated PS81GG.

Characteristics of B.t. PS81GG

Colony morphology—Large colony, dull surface, typical B.t.

Vegetative cell morphology—typical B.t.

Flagellar serotype—3a3b, kurstaki.

Intracellular inclusions—sporulating cells produce a bipyramidal crystal which partially encloses a smaller cuboidal crystal.

Plasmid preparations—agarose gel electrophoresis of plasmid preparations distinguishes B.t. PS81GG from B.t. HD-1 and other B.t. isolates.

Alkali-soluble proteins—B.t. PS81GG has a 130,000 dalton protein and a 60,000 dalton protein.

Unique toxin—the 130,000 dalton toxin is different from any previously identified.

Activity—B.t. PS81GG kills all Lepidoptera tested, and is twice as active against Beet Armyworm as B.t. HD-1.

Beet Armyworm assay results:

B.t. PS81GG LC50=4 ug/ml

B.t. HD-1LC50=8 ug/ml

*Spodoptera exigua* Bioassay: Dilutions are prepared of a spore and crystal pellet, mixed with U.S.D.A. Insect Diet (Technical Bulletin 1528, U.S. Department of Agriculture), and poured into small plastic trays. Neonate *Spodoptera exigua* larvae are placed on the diet mixture and held at 25° C. Mortality is recorded after six days.

*B. thuringiensis* PS81GG, NRRL B-18425, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. B.t. PS81GG, and mutants thereof, can be used to control lepidopteran pests.

A subculture of B.t. PS81GG and the *E. coli* host harboring the toxin gene of the invention, *E. coli* NRRL B-18428 was deposited in the permanent collection of the Northern Research Laboratory, U.S. Department of Agriculture, Peoria, Ill., U.S.A. on Oct. 19, 1988. The accession numbers are as follows: B.t. PS81GG-NRRL B-18425; deposited Oct. 11, 1988. *E. coli* (pMYC388)—NRRL B-18428; deposited Oct. 19, 1988.

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serfaria marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing the B.t. gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed- The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serfaria, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtills*, and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include theological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from abut 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81GG can be made by procedures well known in the art. For example, an asporogenous mutant can be obtained through ethylmethane sulfonate (EMS) mutagenesis of PS81GG. Other mutants can be made using ultraviolet light and nitrosoguanidine by procedures well known in the art.

Following are examples which illustrate procedures, including the best mode, for practicing the invention. These examples should not be construed as limiting. All percentages are by weight and all solvent mixture proportions are by volume unless otherwise noted.

Example 1 —Culturing B.t. PS81GG, NRRL B-18425

A subculture of B.t. PS81GG, NRRL B-18425, or mutants thereof, can be used to inoculate the following medium, a peptone, glucose, salts medium.

| | |
|---|---|
| Bacto Peptone | 7.5 g/l |
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | |
| CaCl$_2$.2H$_2$O | 3.66 g |
| pH 7.2 | |

The salts solution and CaCl$_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

Example 2 —Cloning of Novel Toxin Gene and Transformation into *Escherichia coli*

Total cellular DNA was prepared by growing the cells of *B. thuringiensis* HD-1 and the novel B.t. PS81GG to a low optical density ($OD_{600}=1.0$) and recovering the cells by centrifugation. The cells were protoplasted in TES buffer (30 mM Tris-Cl, 10 mM EDTA, 50 mM NaCl, pH=8.0) containing 20 % sucrose and 50 mg/ml lysozyme. The protoplasts were lysed by addition of SDS to a final concentration of 4%. The cellular material was precipitated overnight at 4° C. in 100 mM final concentration neutral potassium chloride. The supernate was phenol/chloroform (1:1) extracted twice and the DNA precipitated in ethanol. The DNA was purified by isopycnic banding on a cesium chloride gradient.

Total cellular DNA from PS81GG and HD-1 was digested with EcoRI and separated by electrophoresis on a 0.8% Agarose-TAE-buffered gel. A Southern blot of the gel was probed with the NsiI to NsiI fragment of toxin gene contained in the plasmid pM1, 130-7 of NRRL B-18332 and the NsiI to KpnI fragment of the "4.5 Kb class" toxin gene (Kronstad and Whirely, [1986]Gene USA 43: 29–40 ). These two fragments were combined and used as the probe. Results show that hybridizing fragments of PS81GG are distinct from those of HD-1. Specifically, a 3.0 Kb hybridizing band in PS81GG was detected instead of the 800 bp larger 3.8 Kb hybridizing band seen in HD-1.

Two hundred micrograms of PS81GG total cellular DNA was digested with EcoRI and separated by electrophoresis on a preparative 0.8% Agarose-TAE gel. The 2.5 to 3.5 Kb region of the gel was cut out and the DNA from it was electroeluted and concentrated using an ELUTIP TM -d (Schleicher and Schuell, Keene, N.H.) ion exchange column. The isolated EcoRI fragments were ligated to LAMBDA ZAP TM EcoRI arms (Stratagene Cloning Systems, La Jolla, Calif.) and packaged using GIGAPACK GOLD TM extracts. The packaged recombinant phage were plated out with *E. coli* strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BLUESCRIPT TM (Stratagene) plasmid was automatically excised and packaged. The "phagemid" was re-infected in XL1-*Blue E. coli* cells (Stratagene) as part of the automatic excision process. The infected XL1-Blue cells were screened for ampicillin resistance and the resulting colonies were analyzed by standard miniprep procedure to find the desired plasmid. The plasmid, pM4,31-1, contained an approximate 3.0 Kb EcoRI insert which contained an internal EcoRI site. The cloned fragment was sequenced using Stratagene's T7 and T3 primers plus a set of existing B.t. endotoxin oligonucleotide primers.

Total cellular PS81GG DNA was partially digested with AluI or RsaI and digests were mixed. DNA was modified with EcoRI methylase, EcoRI linkers were ligated onto ends, and excess linkers were removed by EcoRI digestion. DNA was size-fractionated on 0.8% Agarose-TAE gels and the approximately 4 to 8 Kb fragments were recovered by electroelution and NACS 52 column chromatography (BRL). Following insert ligation into LAMBDA ZAP TM (Stratagene) which was cut with EcoRI, DNA was packaged into phage heads. Libraries were screened by nucleic acid filter hybridization using a radiolabeled synthetic oligonucleotide probe (CCTGTCGGTTTTTCGGGGCC).

Hybridizing positives were plaque-purified and insert DNA was excised from phage DNA onto pBLUESCRIPT TM plasmid (Stratagene) with helper phage, according to manufacturers directions (Stratagene). The desired plasmid, pMYC388, was restriction mapped and the B.t. toxin coding sequence fully characterized by DNA sequencing.

Data from standard insect tests show that the novel B.t. PS81GG is active against all Lepidoptera tested.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

Plasmid pMYC388 containing the B.t. toxin gene, can be removed from the transformed host microbe by use of standard well-known procedures. For example, *E. coli* (pMYC388) NRRL B-18428 can be subjected to cleared lysate isopycnic density gradient procedures, and the like, to recover pMYC388.

Example 3—Insertion of Toxin Gene Into Plants

The novel gene coding for the novel insecticidal toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

Example 4—Cloning of Novel *B. thuringiensis* Gene Into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Sumers, M. D. and Fraser, M. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequence encoding the novel B.t. toxin gene is shown in SEQ ID NO. 1. The deduced amino acid sequence is shown in SEQ ID NO. 2.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W — C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M = A, C or T The above shows that the novel amino acid sequence of the B.t. toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

We claim:

1. Isolated toxin active against lepidopteran insects consisting essentially of the amino acid sequence shown in SEQ ID NO. 2.

2. A method for controlling lepidopteran insects which comprises administering to said insects or to the environment of said insects a microorganism transformed to express a B.t. toxin consisting essentially of the amino acid sequence shown in SEQ ID NO. 2.

3. A method according to claim 2, wherein said administration is to the rhizosphere.

4. A method according to claim 2, wherein said administration is to the phylloplane.

5. An insecticidal composition comprising insecticide containing substantially intact, treated cells having prolonged pesticidal activity when applied to the environment of a target pest, wherein said insecticide is a polypeptide toxic to lepidopteran insects, is intracellular, and is produced as a result of expression of a transformed microbe capable of expressing the B.t. toxin having the amino acid sequence shown in SEQ ID NO. 2.

* * * * *

UNITED STATES PATENT AND TRADEMARK OFFICE
CERTIFICATE OF CORRECTION

PATENT NO. : 5,352,661
DATED : October 4, 1994
INVENTOR(S) : Jewel Payne, et al

It is certified that error appears in the above-indentified patent and that said Letters Patent is hereby corrected as shown below:

Column 1, line 23: Delete "Whirely" and insert --Whitely--.
Column 4, line 27: Delete "Serfaria marcescens," and insert --Serratia marcescens,--.
Column 5, line 25: Delete "or transformed-" and insert --or transformed.--
Column 6, line 56: Delete "Serfaria," and insert --Serratia,--.
Column 8, line 10: Delete "theological agents," and insert --rheological agents--.
Column 9, line 24: Delete "Whirely," and insert --Whitely,--.

Signed and Sealed this

Twentieth Day of December, 1994

Attest:

BRUCE LEHMAN

Attesting Officer     Commissioner of Patents and Trademarks